United States Patent
Arai et al.

[11] Patent Number: 5,865,725
[45] Date of Patent: Feb. 2, 1999

[54] IMAGE CAPTURE INSTRUMENT WITH SIDE VIEW ANGLE

[75] Inventors: Junichi Arai; Kazuhisa Shimada; Kouichi Watanabe, all of Urawa, Japan

[73] Assignee: Moritex Corporation, Japan

[21] Appl. No.: 780,800

[22] Filed: Jan. 9, 1997

Related U.S. Application Data

[63] Continuation of Ser. No. 527,416, Sep. 13, 1995, abandoned.

[51] Int. Cl.⁶ .................................................. A61B 1/00
[52] U.S. Cl. .......................... 600/176; 600/169; 600/170; 600/175
[58] Field of Search .................................. 600/167, 168, 600/169, 170, 172, 173, 174, 175, 176, 182; 433/29, 30, 31

[56] References Cited

U.S. PATENT DOCUMENTS

| | | | |
|---|---|---|---|
| 3,279,460 | 10/1966 | Sheldon | 600/169 |
| 3,417,745 | 12/1968 | Sheldon | 600/176 |
| 4,076,018 | 2/1978 | Heckele | 600/169 |
| 4,706,653 | 11/1987 | Yamamoto | 600/175 |
| 4,858,001 | 8/1989 | Milbank et al. | 600/170 |
| 4,941,457 | 7/1990 | Hasegawa | 600/175 |
| 5,016,098 | 5/1991 | Cooper | 600/129 |
| 5,325,847 | 7/1994 | Matsuno | 600/170 |
| 5,518,501 | 5/1996 | Oneda et al. | 600/175 |

FOREIGN PATENT DOCUMENTS

| | | | |
|---|---|---|---|
| 53237 | 4/1912 | Austria | 600/170 |
| 87254 | 4/1956 | Norway | 600/174 |

*Primary Examiner*—Gene Mancene
*Assistant Examiner*—Ira Hatton
*Attorney, Agent, or Firm*—Brown, Martin, Haller & McClain, LLP

[57] ABSTRACT

The present invention is characterized by arranging along the lengthwise direction within a lens barrel: a side view mirror or prism which reflects in the lengthwise direction of said lens barrel the optical image incident from a translucent window that opens to the tip side surface; an image focusing optical system which focuses that optical image; and a CCD element which captures the optical image focused by said image focusing optical system; and is characterized by mounting in the light route reaching from aforementioned side view mirror or prism to said CCD element optical image inversion mirror or prism which reflects the optical image inverted by said side view mirror or prism such that it faces said CCD element in a reinverted state.

11 Claims, 2 Drawing Sheets

IMAGE CAPTURE INSTRUMENT WITH SIDE VIEW ANGLE

This is a continuation of application Ser. No. 08/527,416, filed Sep. 13, 1995, now abandoned.

BACKGROUND OF THE INVENTION

1. Field of the Invention

The present invention is related to a side view image input device which is used as an internal examination scope found in dental scopes and equipment.

2. Description of the Related Art

There have been proposals for side view dental scopes for dental treatment which make visible the status of any tooth and gum portion positioned within the oral cavity in locations which are difficult to see; and a CCD element is incorporated for taking photographs of this.

In this type of dental scope, a light projection window forms an opening to the tip side surface of a lens barrel; and arranged along the optical axis are: a side view mirror, which reflects the optical image incident from a side translucent part to face the lengthwise direction of the lens barrel; an image focusing optical system, which focuses that image by a specified magnification; and a CCD element, which captures the optical image focused by that image focus optical system. In addition, industrial side view type scopes also have the same structure.

Then, when used as a dental scope, if the lens barrel is inserted into the oral cavity, etc. and the translucent window is made to face the location to be seen, an image of part of the teeth or gums can be photographed by the CCD element, and therefore this can be projected on a television monitor.

Nonetheless, in this situation, because it is necessary to bend the light route at a right angle utilizing the reflection of the side view mirror or a prism in order to see the side surface of the lens barrel, the image which is projected onto the television monitor is inverted top to bottom, left to right, and there is the concern that the user will experience an optical illusion.

Moreover, once the image signal obtained by processing the signal that is output from the CCD element is memorized, if the left and right of the image is inverted by reversing them synchronously with the horizontal scan signals, the correct image can be projected on the television monitor without left to right inversion, but there are the problems that that image signal inversion circuit is complicated, and the costs are increased.

SUMMARY OF THE INVENTION

Thus, the present invention takes up the technical problem of being able to project the correct image that has no top to bottom, left to right reversed images by an extremely simple means and without using an image signal inversion circuit which increases costs.

In order to solve these problems, the present invention is characterized by arranging along the lengthwise direction in a lens barrel a side view mirror or prism which reflects an optical image incident from a translucent window that opens to the side surface of the tip facing the lengthwise direction of that lens barrel, an image focusing optical system that focuses that optical image and a CCD element which captures the optical image that is focused by said image focusing optical system; and is characterized by mounting in the light route that reaches from the aforementioned side view mirror or prism to the CCD element an optical image inversion mirror or prism which reflects the optical image inverted by said side view mirror or prism such that it faces the CCD element in a reinverted state.

According to the present invention, because an optical image inversion mirror or prism is arranged between the side view mirror or prism and the CCD element in order to prevent the image, incident from the translucent window that opens to the side of the lens barrel tip and reflected by a mirror or prism for side viewing, from passing through the image focusing optical system and being photographed by the CCD element in a state that is inverted top to bottom and left to right, the optical image inverted by the side view mirror or prism is reinverted, and the positive image is photographed by the CCD element.

Consequently, the monitor image is projected in the same direction as directly viewed by the eyes, without being inverted top to bottom, and left to right.

BRIEF DESCRIPTION OF THE DRAWINGS

The present invention will be better understood from the following detailed description of preferred embodiments of the invention, taken in conjunction with the accompanying drawings, in which like reference numerals refer to like parts, and in which.

DETAILED DESCRIPTION OF THE PREFERRED EMBODIMENTS

Figure 5:
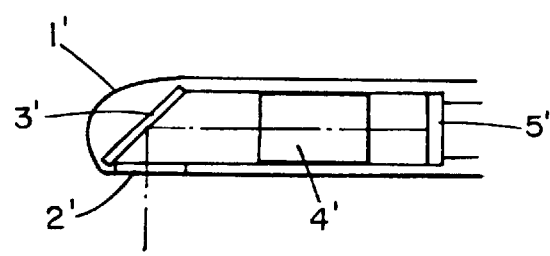
FIG. 5 illustrates a prior art side view image device.

FIG. 5 illustrates a prior art dental scope in which a lens barrel 1' has a window 2' facing to one side. Side view mirror 3' reflects the optical image along the longitudinal axis of the lens barrel, and the image is focused by image focusing system 4' and captured by CCD element 6'. This has the disadvantage that the image is inverted.

Figure 1:
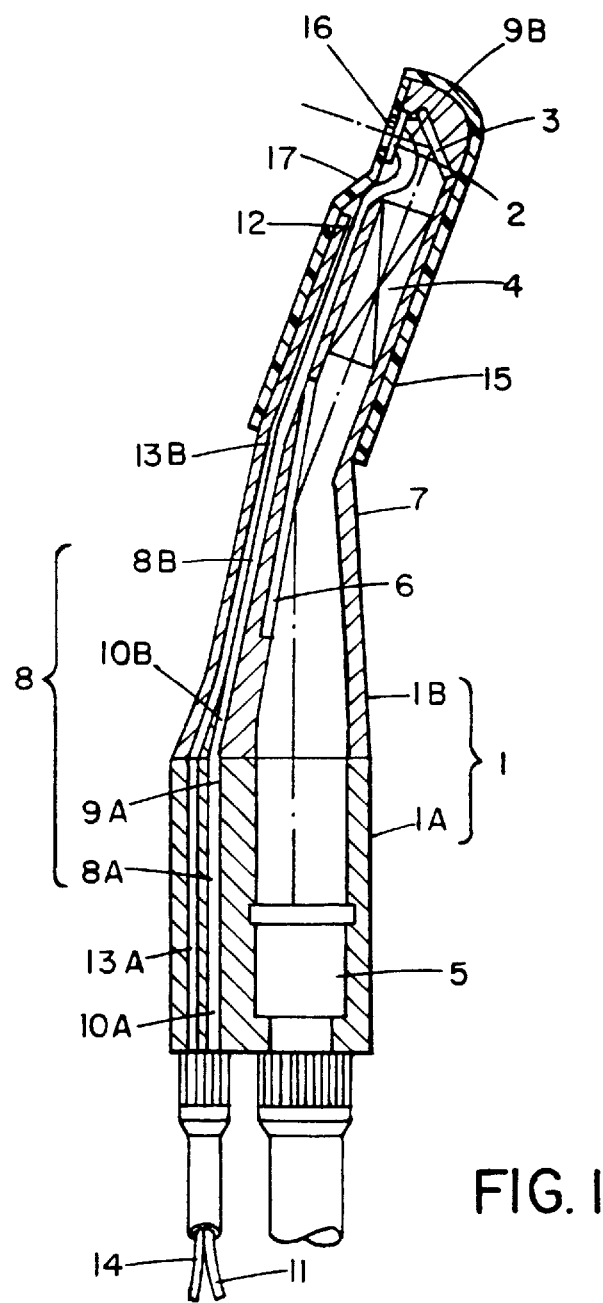
FIG. 1 is a cross-sectional diagram indicating one example of a side view image input device related to the present invention.
Figure 2:
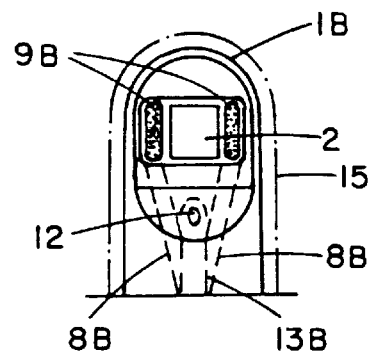
FIG. 2 is a front view diagram indicating an enlargement of the tip part.

FIGS. 1 and 2 illustrate a side view image device according to a first embodiment of the invention which is used as a dental scope, and arranged along the lengthwise direction within lens barrel 1 are: side view mirror 3, by which the optical image incident from translucent window 2 that opens to the side of the tip is reflected in the lengthwise direction of said lens barrel 1; image focusing optical system 4 which focuses that optical image at the specified magnification; and CCD element 5 which captures that optical image which is focused by said optical system 4.

Then, optical image inversion mirror 6, which reflects the optical image inverted by side view mirror 3 to face CCD element 5 in a state which has returned to the normal image by being reinverted, is mounted in the light route reaching from image focusing optical system 4 to CCD element 5.

Moreover, aforementioned lens barrel 1 comprises image capture part 1A which incorporates CCD element 5, and optical head 1B which is installed to be attachable/detachable on that tip; and the lens barrel is bent in the same angular shape as the tip part of a dental drill so that every nook and corner within the oral cavity can be seen when inserted in the oral cavity.

Side view mirror 3 is arranged on the inside of translucent window 2 formed on the tip of said optical head 1B such that it is, for example, at 45° in relation to the optical axis of image focusing optical system 4, and the optical image incident from aforementioned translucent window 2 bends at 90° to face the lengthwise direction of lens barrel 1.

Then, optical image inversion mirror 6 is arranged on the inside of bend 7 which is bent at an angle such that, for example, it becomes an incident angle of 10°, and is reflected to face CCD element 5 by the optical axis being bent approximately 20° following the lengthwise direction of optical head 1B.

In addition, because image focusing optical system 4 is arranged in the space between aforementioned mirrors 3 and 6, optical head 1B and the entire lens barrel 1 are not longer than necessary, and can be designed to be compact; moreover, because it is designed such that the specified magnification can be enlarged or contracted, the magnification of the optical image can be modified by exchanging this optical head 1B.

Bundled fibers 8 lead light for illumination up to translucent window 2. Bundled fibers 8 comprise fibers 8A which are provided on image capture part 1A, and bundled fibers 8B which are provided on optical head 1B. Bundled fibers 8A and 8B are optically connected.

Bundled fibers 8B which are provided in optical head 1B are arranged such that their tips 9 emit light facing the subject by being directed both up and down the side of translucent window 2 as, for example, indicated in FIG. 2. In addition, the shape of tips 9b of bundled fibers 8B may be optionally selected in the arrangement of a circle around the perimeter of translucent window 2.

Moreover, the tips 9a of bundled fibers 8A which are provided on image capture part 1A are arranged to face the back ends 10b of aforementioned bundled fibers 8B, and the other end 10a is connected to the light source (not indicated in the diagram) through optical fiber cable 11.

Air spray outlet 12 sprays air onto the surface of translucent window 2 so that it does not become cloudy when optical head 1B has been placed in the oral cavity. This outlet is connected to an air pump (not indicated in the diagram) through air hose 14 that is connected in lens barrel 1 by air supply pipes 13A and 13B which are formed on optical head 1B and image capture part 1A.

Furthermore, 15 is a cover that covers the part of optical head 1B that is inserted in the oral cavity, and is formed, for example, of plastic, and can be used interchangeably with disinfected covers by removing said cover 15 each time the device is used. Then, the used cover may either by disinfected and reused, or used and disposed.

With this cover 15, the part that covers aforementioned translucent window 2 and tips 9a of bundled fibers 8B are formed into transparent translucent part 16, and the part which covers air spray outlet 12 is formed into air passage hole 17.

The above is one example of a configuration of the present invention, and next, its operation will be explained.

First, with optical head 1B mounted on image capture part 1A, when the light source is turned on, that light is irradiated from tips 9a of bundled fibers 8A facing the front of translucent window 2.

Then, when image capture part 1A is held in the hand and the tip of optical head 1B is inserted in the oral cavity and light projection window 2 is made to face the place to be viewed, the subject is illuminated by the light irradiated from tip 9b of bundled fibers 8B.

Then, the optical image incident from translucent window 2 is reflected by side view mirror 3 along the lengthwise direction of lens barrel 1. This passes through lens 4 in a left to right inverted state, and the image is captured by CCD element 5.

At this time, because an optical image inversion mirror is arranged between lens 4 and CCD element 5, the optical image inverted by side view mirror 3 is reinverted, and the positive image is taken by CCD element 5.

Consequently, if this is projected on a television monitor (not indicated in the diagram), that image is not inverted left to right or top to bottom, and is projected in the same direction as when directly viewed with the eyes.

Moreover, if optical head 1B is covered with cover 15, even if blood from the patient, etc. becomes attached, the device can be used hygienically to prevent infectious disease by replacing the cover with a new one.

Additionally, when spraying air from air spray outlet 12, because air is sprayed directly on the surface of translucent window 2 if protective cap 15 is not used, or, because air is sprayed on translucent part 16 from air spray hole 17 if protective cap 15 is used, translucent window 2 and light projection part 16 do not become clouded by the moisture expired by the patient.

Figure 3:
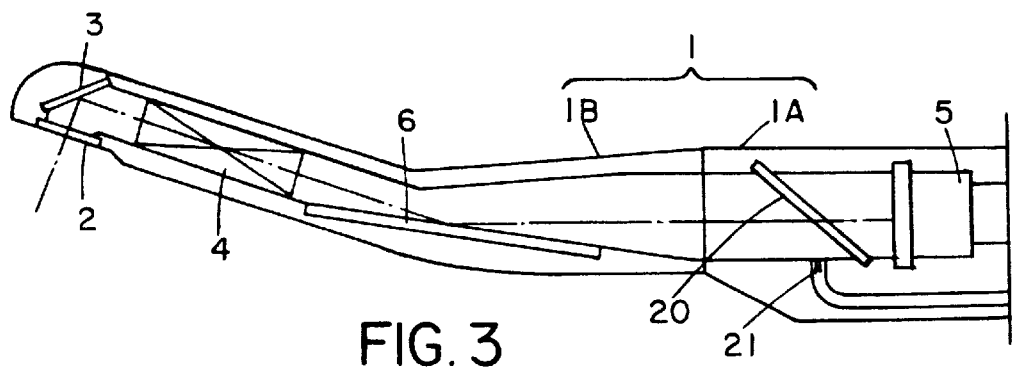
FIGS. 3 and 4 are cross-sectional diagrams indicating other embodiments.

FIG. 3 is a cross-sectional diagram indicating another embodiment. In this example, the illumination light is not led up to the translucent window by bundled fibers, but rather half mirror 20 is mounted on the optical axis by which light is incident on CCD element 5 of image capture part 1A, and coaxial objective illumination is conducted by irradiating the illumination light on that half mirror 20 using bundled fibers 21.

If this is done, the structure of optical head 1B can be simplified even more.

Figure 4:
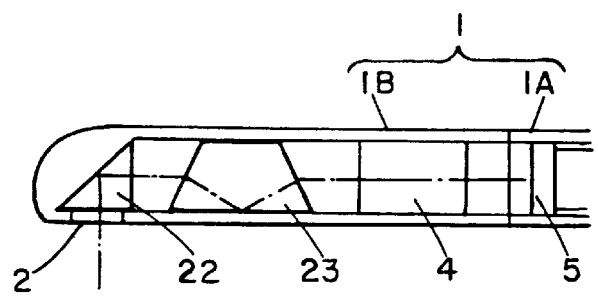

In addition, FIG. 4 arranges side view prism 22 and optical image inversion prism 23 by substituting for side view mirror 3 and optical image inversion mirror 6. In particular, optical image inversion prism 23 is arranged between side view prism 22 and image focusing optical system 4.

Side view prism 22 uses a triangular prism, and optical image inversion prism 23 uses a trapezoid prism.

With this optical inversion prism 23, because the direction of the incident optical axis and the direction of the exit optical axis do not change, the optical image can be easily inverted even if optical head 1B is formed in a straight line.

In addition, not only is it possible to use optional combinations of side view mirror 3 or side view prism 22, and optical image inversion mirror 6 or optical image inversion prism 23, but also the set angles for these are not limited to this embodiment, and can be optionally set corresponding to the diffraction angle of the incident optical axis.

Moreover, the present invention is not limited to use in dental scopes, and can also be used in medical endoscopes, and industrial investigative scopes for the purpose of viewing the insides and gaps in devices and machinery.

Furthermore, an explanation was given of a case in which lens barrel 1 can be separated into image capture part 1A and optical head 1B, but because detachment is not necessary when no particular modifications of magnification are required, these may also be formed into a single body.

As described above, according to the present invention, the optical image incident from the translucent window that opens to the side surface of the tip of the lens barrel is inverted left to right and top to bottom when reflected by a side view mirror or prism, and is captured by a CCD element after passing through an image focusing optical system, but because an optical image inversion mirror or prism is arranged between the image focusing optical system and the CCD element, the optical image reflected by the side view mirror or prism is reinverted, and because the positive image is captured by the CCD element, a complicated inversion circuit, etc. is not used, and there is the superior effect that a positive image without reversal can be projected on a monitor screen by an extremely simple means.

Although some preferred embodiments of the invention have been described above by way of example only, it will be understood by those skilled in the field that modifications may be made to the disclosed embodiments without departing from the scope of the invention, which is defined by the appended claims.

We claim:

1. A side view image input device, comprising:

a lens barrel having a central axis and a tip at one end of the barrel;

the barrel having a translucent window adjacent said tip and facing said central axis;

an image reflecting member positioned in said barrel facing said window to reflect an inverted light image incident from said window along the central axis of said barrel;

an image focusing optical system for focusing the inverted light image reflected from said reflecting member along a light path in said barrel;

a CCD element positioned in said barrel to receive the focused light image from said optical system; and only one optical element located in said light path between said image focusing optical system and CCD element, the optical element comprising a single optical image inverting member mounted in said lens barrel in said light path for reflecting and re-inverting the light image whereby the image faces said CCD element in an upright, re-inverted state.

2. The device as claimed in claim 1, wherein the image reflecting member is a side view mirror.

3. The device as claimed in claim 1, wherein the image reflecting member is a side view prism.

4. The device as claimed in claim 1, wherein the optical image inverting member comprises a single optical image inversion mirror.

5. The device as claimed in claim 1, wherein the optical image inverting member comprises an optical image inversion prism.

6. A side view image input device, comprising:

a lens barrel having a central axis and a tip at one end of the barrel;

the barrel comprising an image capture part and an elongated optical head part releasably secured to said image capture part, the optical head part of the barrel including said tip;

the optical head part of the barrel having a translucent window adjacent said tip and facing said central axis;

an image reflecting member positioned in said optical head part of said barrel facing said window to reflect an inverted image incident from said window along the central axis of said barrel;

an image focusing optical system in the optical head part of said barrel for focusing the inverted image reflected from said reflecting member along a light path in said barrel;

a CCD element positioned in the image capture part of said barrel to receive the focused image from said optical system;

a single optical image inverting member mounted in said optical head part of said barrel in said light path after said image focusing optical system for reflecting and re-inverting the image before the image reaches said CCD element, whereby the image faces said CCD element in an upright, re-inverted state; and the light path including a first portion in said optical head part and a second portion in said image capture part of said barrel, the first portion of said light path being longer than the second portion.

7. The device as claimed in claim 1, including bundled fibers installed along the length of the lens barrel up to said window for providing illumination.

8. The device as claimed in claim 1, wherein said barrel has an air supply bore extending along the lengthwise direction of said barrel and having an air spray outlet facing said window for spraying air onto the window.

9. The device as claimed in claim 1, including an attachable/detachable cover for covering the tip of said barrel and said translucent window, at least part of said cover which is positioned over the translucent window of the barrel being translucent.

10. The device as claimed in claim 1, wherein the lens barrel has a bend defining first and second barrel portions at an angle to each other, and the image inverting member is mounted at the bend.

11. The device as claimed in claim 1, wherein said image focusing optical system is located in said light path between said image reflecting member and image inverting member.

* * * * *